(12) United States Patent
Arcilla et al.

(10) Patent No.: US 7,565,906 B2
(45) Date of Patent: Jul. 28, 2009

(54) PRESSURE/FLOW CONTROL VALVE AND SYSTEM USING SAME

(75) Inventors: Mabini M Arcilla, San Diego, CA (US); Mehdi M Jafari, Laguna Hills, CA (US); Patrick Nguyen, Carlsbad, CA (US)

(73) Assignee: RIC Investments, Inc., Wilmington, DE (US)

( * ) Notice: Subject to any disclaimer, the term of this patent is extended or adjusted under 35 U.S.C. 154(b) by 470 days.

(21) Appl. No.: 10/832,184

(22) Filed: Apr. 26, 2004

(65) Prior Publication Data

US 2004/0211422 A1  Oct. 28, 2004

Related U.S. Application Data

(60) Provisional application No. 60/465,981, filed on Apr. 28, 2003.

(51) Int. Cl.
- *F16K 1/08* (2006.01)
- *A61M 15/00* (2006.01)
- *A61M 16/00* (2006.01)
- *A62B 9/02* (2006.01)

(52) U.S. Cl. .................. 128/204.19; 128/200.24; 128/204.18; 128/205.24

(58) Field of Classification Search ............ 128/200.24, 128/204.18, 204.19, 204.23, 205.24; 137/315.03, 137/599.07, 909; 251/65, 64
See application file for complete search history.

(56) References Cited

U.S. PATENT DOCUMENTS

| | | | |
|---|---|---|---|
| 3,581,742 A * | 6/1971 | Glenn .................. | 128/204.19 |
| 3,831,595 A * | 8/1974 | Valenta et al. ......... | 128/202.22 |
| 3,877,478 A * | 4/1975 | Longworth .................. | 137/94 |
| 4,838,257 A * | 6/1989 | Hatch ..................... | 128/204.18 |
| 4,838,527 A | 6/1989 | Hatch | |
| 5,127,400 A | 7/1992 | DeVries | |
| 5,148,802 A | 9/1992 | Sanders et al. | |
| 5,313,937 A | 5/1994 | Zdrojkowski | |
| 5,433,193 A | 7/1995 | Sanders et al. | |
| 5,490,499 A * | 2/1996 | Heinonen et al. ...... | 128/203.28 |
| 5,632,269 A | 5/1997 | Zdrojkowski | |
| 5,685,296 A | 11/1997 | Zdrojkowski et al. | |
| 5,803,065 A | 9/1998 | Zdrojkowski et al. | |
| 6,029,664 A | 2/2000 | Zdrojkowski et al. | |
| 6,189,532 B1 * | 2/2001 | Hely et al. ............. | 128/205.24 |
| 6,526,970 B2 * | 3/2003 | DeVries et al. ........ | 128/204.21 |
| 6,536,432 B2 | 3/2003 | Truschel | |
| 6,604,497 B2 * | 8/2003 | Buehrle et al. ........... | 123/90.12 |

(Continued)

FOREIGN PATENT DOCUMENTS

WO  WO 98/26830  * 6/1998

*Primary Examiner*—Justine R Yu
*Assistant Examiner*—Annette F Dixon

(57) ABSTRACT

A pressure/flow control valve that includes a first valve member and a second valve member moveable relative to one another and cooperating with one another so as to define a valve opening having a size that varies with a relative position between these members. The first magnet is operatively coupled to the first valve member and a second magnet is operatively coupled to the second valve member and magnetically coupled to the first magnet. The first and second magnets are disposed such that a repulsive force between them increases asymptotically as the magnets move together, thereby providing a dampening force between the first and second valve members that allows these valve members to be moved rapidly from one position to the next in a highly controlled fashion.

22 Claims, 5 Drawing Sheets

U.S. PATENT DOCUMENTS 6,615,831 B1 * 9/2003 Tuitt et al. ............. 128/204.18
6,626,175 B2   9/2003 Jafari et al.
6,920,875 B1   7/2005 Hill et al.
2004/0103780 A1 * 6/2004 Shteynberg ................... 92/82

* cited by examiner

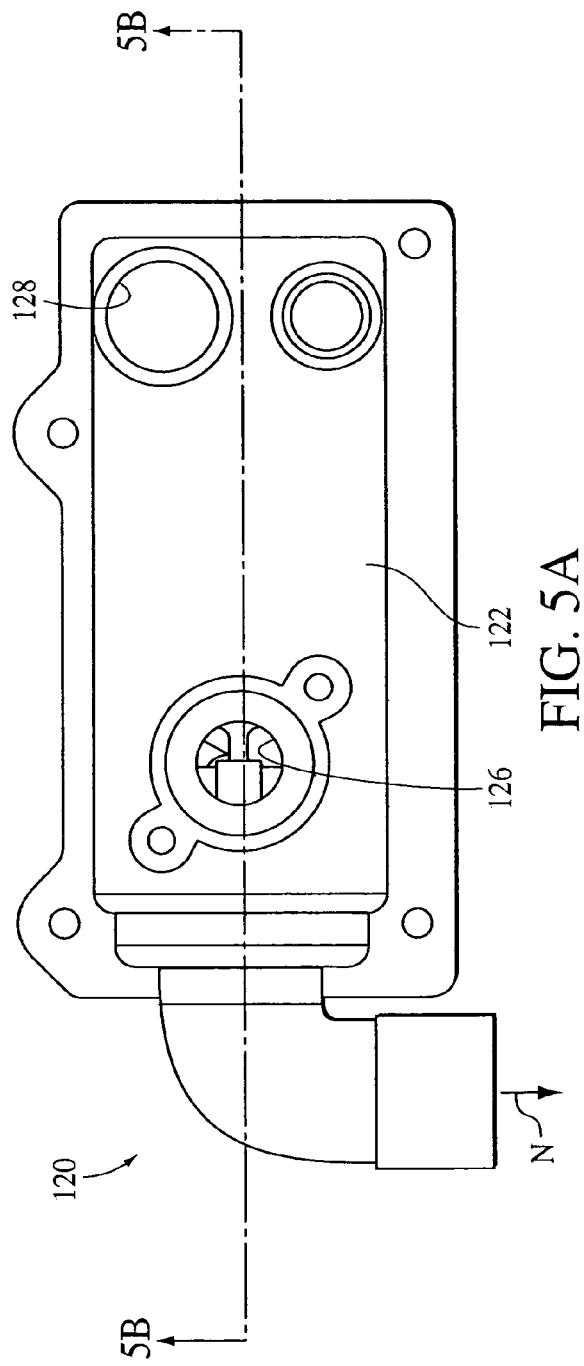
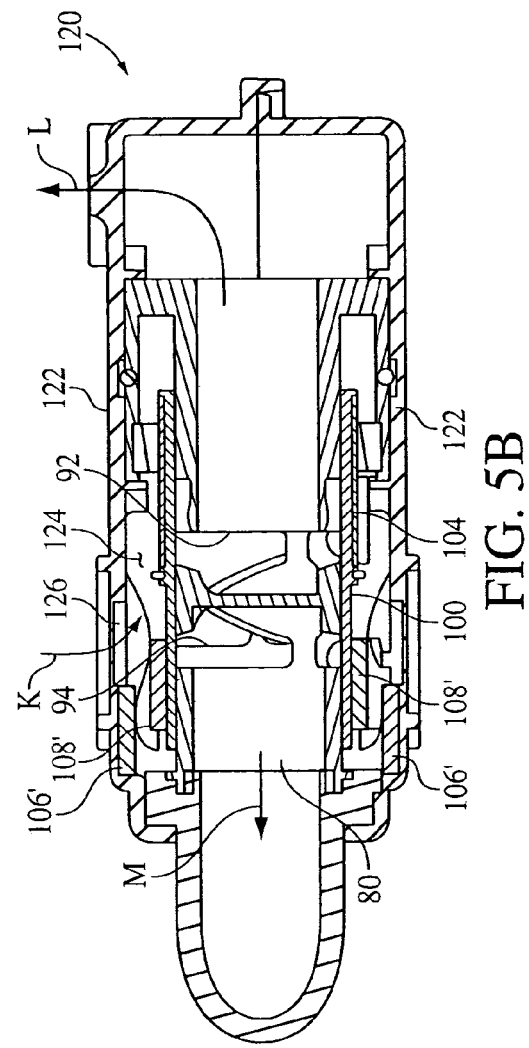
FIG. 5A
FIG. 5B

PRESSURE/FLOW CONTROL VALVE AND SYSTEM USING SAME

CROSS-REFERENCE TO RELATED APPLICATIONS

This application claims priority under 35 U.S.C. § 119(e) from provisional U.S. patent application No. 60/465,981 filed Apr. 28, 2003 the contents of which are incorporated herein by reference.

BACKGROUND OF THE INVENTION

1. Field of the Invention

The present invention pertains to a pressure/flow control valve for use in a fluid delivery system, and, in particular, to a pressure/flow control valve whose movement is dampened non-linearly to improve valve response and controllability in the fluid delivery system.

2. Description of the Related Art

There are numerous situations where it is desirable to control the flow of fluid through a conduit. For example, in the medical field, a flow of gas is delivered to a patient by a conventional mechanical ventilator to supplement or replace the patient's own respiration. It is necessary to control the flow and/or pressure of gas delivered to the patient so that proper volume and/or pressure of gas is provided by the ventilator to the patient at the proper time.

Other fluid delivery systems are known for providing a flow of gas to an airway of a patient at an elevated pressure to treat a medical disorder. For example, it is known to use a continuous positive airway pressure (CPAP) device to supply a constant positive pressure to the airway of a patient to treat obstructive sleep apnea (OSA). It is also known to use a fluid delivery system to provide a bi-level positive pressure therapy in which the pressure of gas delivered to the patient varies with the patient's breathing cycle or varies with the patient's effort to increase the comfort to the patient. It is further known to provide an auto-titration positive pressure therapy in which the pressure provided to the patient changes based on the detected conditions of the patient, such as whether the patient is snoring or experiencing an apnea, hypopnea or upper airway resistance.

Conventional fluid delivery systems, which include medical ventilators, CPAP, bi-level, and auto-titrating systems (and variants thereof), typically include a pressure generator, for example, a blower, piston, or bellows, that creates a flow of breathing gas at a pressure greater than the ambient atmospheric pressure. A patient circuit delivers the elevated pressure breathing gas to the airway of the patient. Typically, the patient circuit includes a conduit, e.g., a single limb or lumen, having one end coupled to the pressure generator and a patient interface device coupled to the other end of the conduit. The patient interface connects the conduit with the airway of the patient so that the elevated pressure gas flow is delivered to the patient's airway. In a closed system, e.g., when providing ventilation to the patient, a second limb or lumen is provided that couples the patient interface with an exhaust valve. In all of these pressure support therapies and patient ventilation techniques, as well as many not mentioned, it is important to control the pressure or the flow of gas delivered to the patient through the patient circuit.

In a typical fluid delivery system, a valve is provided to control the pressure and/or flow of gas delivered by the pressure generator to the patient. Typically, the valve is provided downstream of the pressure generator in, or associated with, the fluid carrying patient circuit. In some conventional systems, the valve provides a variable sized restriction to the flow of fluid through the conduit. It is also known to divert or exhaust gas from the patient circuit using a variable orifice valve to control the pressure, and, hence, the flow of gas to the patient. The flow restricting and flow diverting approaches have also been used in combination.

A control system is typically provided to control the actuation of the valve or valves. If capable of operating in synchronization with the patient's respiratory efforts, the control system for the ventilator or fluid delivery system includes the ability to monitor the respiratory effort of the patient and control the actuation of the valve in a feed-back fashion based on this monitoring. For example, a pressure sensor and a flow sensor are typically provided to monitor the pressure and flow in the patient circuit or patient interface to detect when the patient attempts to transition between an inspiratory and an expiratory phase of the breathing cycle. When a transition is detected, a controller causes the pressure/flow control valve to open or close accordingly.

It can be appreciated that the valve must be able to react quickly to detected changes in the patient respiration so that a transition in pressure or flow is provided immediately upon detecting the change in respiratory state. In addition, the valve must be able to accurately move to its operating position to ensure that the proper pressure and/or flow is delivered to the patient.

It is known in some conventional pressure/flow control valves to provide feedback information, such as the position, speed, or acceleration of the moving component of the valve relative to the stationary component, to assist in controlling the operation of the valve. However, this type of feedback control increases the complexity of the valve and does not provide maximum response time, as the position of the valve must be continuously monitored and controlled in a feedback fashion, thereby slowing down its actuation time. Therefore, it is desirable to avoid using feedback information in controlling valve movement.

However, it is a challenge to control the position of force-activated actuators in time-variant motion control systems with uncertain system dynamics without utilizing velocity and/or position feedback. In medical ventilators, flow or pressure is regulated by controlling the position (opening area) of a moving member relative to a stationary member in a valve. When the control input to the moving member is force or a force-related parameter, such as a coil current in voice coil valves, accurate positioning of the valve for delivering specific flow or pressure patterns is challenging without velocity and/or position feedback. This task becomes even more challenging in the presence of stick-slip conditions and due to the relatively high acceleration of the moving member, which typically has a small mass. Also, in a pressure generating system, the pattern and rate of valve movement for achieving fixed flow or pressure patterns is dependent on the uncertain, i.e., unmeasured, patient lung dynamics and breathing behavior. These factors and the tight performance requirements for a fluid delivery system, especially a life supporting medical ventilator, demand motion control systems with accurate and fast parameter, i.e., flow and/or pressure regulation.

SUMMARY OF THE INVENTION

Accordingly, it is an object of the present invention to provide a fluid delivery system with a pressure/flow control valve that overcomes the shortcomings of conventional fluid delivery systems. This object is achieved according to one embodiment of the present invention by providing a fluid delivery system that includes a pressure generating system adapted to generate a flow of gas at a pressure level, a patient circuit communicating the pressure generating system with an airway of a patient, and a valve associated with the patient circuit to control the pressure and/or flow of gas in the patient circuit. The valve comprise a first valve member and a second valve member that are moveable relative to one another and that cooperate to define a valve opening having a size that varies with a relative position between the first valve member and the second valve member. A first magnet is operatively coupled to the first valve member, and a second magnet is operatively coupled to the second member and magnetically coupled to the first magnet. By orienting the first and second magnets such that a repulsive force between the first magnet and the second magnet increases asymptotically as the second magnet moves toward the first magnet, the present invention provided a unique dampening force between the first and second valve members that allows these valve members to move rapidly from one position to the next in a highly controlled fashion, i.e., without overshoot when a given amount of actuating force is applied to the moving valve member.

It is a still further object of the present invention to provide a method of controlling pressure or flow delivered to a patient that overcomes the shortcomings of conventional pressure/flow delivery methods. This object is achieved according to one embodiment of the present invention by providing a method of controlling pressure or flow in a fluid delivery system that includes providing a first valve member and a second valve member moveable relative to one another and that together define a valve opening having a size that varies with a relative position between the first valve member and the second valve member to control a pressure or a flow of gas delivered to the patient. The method further includes providing an actuating force on the second valve member to move the second valve member toward the first valve member and controlling movement of the second valve member toward to the first valve member. This is accomplished by providing a dampening force that prevents movement of the second valve member toward the first valve member. More specifically, the dampening force increases non-linearly as the second valve member moves toward the first valve member. As noted above, this non-linear dampening force makes it possible for the valve members to move rapidly from one position to the next in a highly controlled fashion, i.e., without overshoot when a given amount of actuating force is applied to the moving valve member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 5A is a side view of a pressure/flow control valve according to a third embodiment of the present invention, and FIG. 5B is a cross-sectional view of the valve of FIG. 5A, taken along line 5B-5B.

DETAILED DESCRIPTION OF THE PRESENTLY PREFERRED EMBODIMENTS OF THE INVENTION

Figure 1:
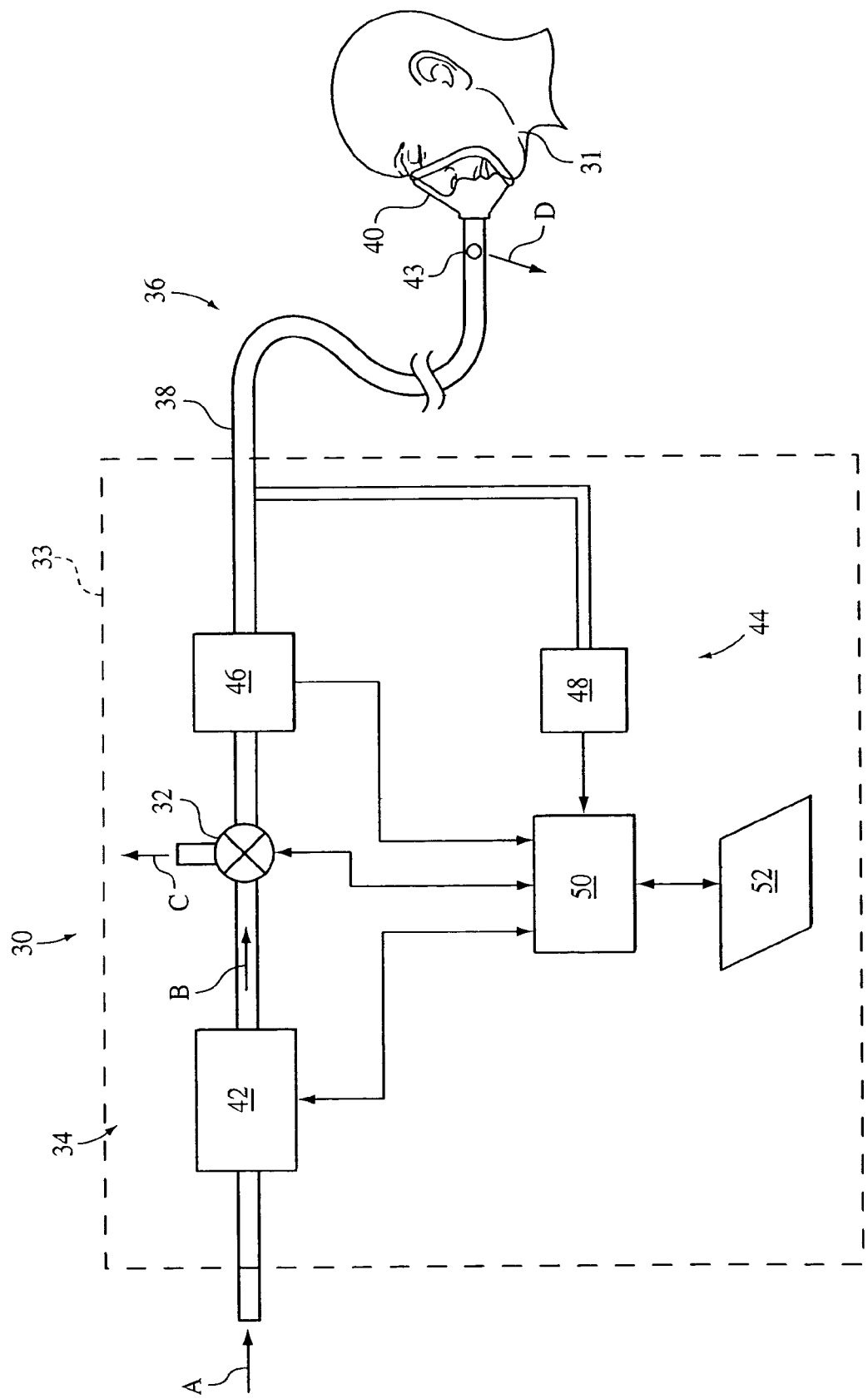
FIG. 1 is a schematic illustration of a fluid delivery system including the pressure/flow control valve of the present invention.

FIG. 1 schematically illustrates an exemplary embodiment of a fluid delivery system 30 that is particularly well suited to use a valve 32 according to the principles of the present invention for controlling the pressure and/or flow of fluid delivered to an airway of a patient. Fluid delivery system 30 is any conventional system for supplying a flow of gas to a patient invasively or non-invasively in which the pressure or the flow delivered to the patient must be controlled. The present invention envisions, for example, that fluid delivery system 30 is a mechanical ventilator (either invasive or non-invasive that control a volume (flow) of gas delivered to a patient) or a positive airway pressure device, such as CPAP, bi-level, or auto-titrating fluid delivery system.

Fluid delivery system 30 includes a pressure/flow generating system, generally indicated at 34, and a patient circuit 36, which includes a conduit 38, and a patient interface device 40. In the illustrated embodiment, pressure/flow generating system 34 includes a pressure/flow generator 42 and pressure/flow control valve 32 located at the outlet of the pressure generator to control the pressure and/or the flow of gas delivered to a patient 31. The components of the fluid delivery system are providing in a housing 33, while conduit 38 extends therefrom.

Pressure/flow generator 42 receives a supply of gas from a breathing gas source, as indicated by arrow A, and outputs the breathing gas, as indicated by arrow B, to patient circuit 36 at a pressure that is greater than atmosphere for delivery to the airway of the patient. In a preferred embodiment of the present invention, pressure/flow generator 42 is a mechanical pressure generator, such as a blower, bellows, or piston, that receives ambient air, for example, at an inlet from the gas source. Pressure/flow control valve 32 controls the pressure of the flow of breathing gas delivered to the patient via the patient circuit by restricting the flow to the patient, by diverting flow from patient circuit 36, as indicated by arrow C, or a combination thereof. It should be noted that the diversion of gas from patient circuit 36 can be made to the ambient atmosphere or to another location along the fluid delivery system, such as to the inlet of pressure/flow generator 42. Optionally, the gas flow delivery system can include a muffler at the inlet or outlet of the pressure generator.

The present invention further contemplates controlling the pressure of the flow of breathing gas delivered to the patient by controlling the operating speed of pressure/flow generator 42 in combination with valve 32. Those skilled in the art can appreciate that other techniques for controlling the pressure of the flow of breathing gas delivered to the patient can be implemented in fluid delivery system 30 using valve 32. For example, multiple pressure/flow restricting valves can be provided in the gas delivery system. One embodiment of the present invention contemplates locating valve 32 upstream of pressure/flow generator 42 to control the flow (arrow A) of gas to pressure/flow generator 42, and, hence, the pressure or the flow of gas output delivered to the patient.

Typically, the source of breathing gas is the ambient atmosphere, where its pressure is subsequently elevated for delivery to the patient by the pressure generating system. It is to be understood, that other sources of breathing gas are contemplated by the present invention, such as oxygen or an oxygen mixture from an oxygen source. It is to be further understood, that the present invention contemplates that pressurized air can be provided to the airway of the patient directly from a tank of pressurized air via the patient circuit without using a pressure generator, such as a blower, bellows or piston, to increase the pressure of the air. Of course, a pressure/flow control valve, such as valve 32, would be required to control the pressure of the gas delivered to the patient. The important feature with respect to the present invention is the control of the pressurized breathing gas via pressure/flow control valve 32, not necessarily the source or manner in which the pressurized breathing gas is generated.

Although not shown in FIG. 1, the present invention also contemplates providing a secondary flow of gas, either alone or in combination with the primary flow of gas (arrow A) from atmosphere. For example, a flow of oxygen from any suitable source can be provided upstream to pressure/flow generator 42 or downstream of the pressure/flow generator in the patient circuit or at the patient interface device to control the fraction of inspired oxygen delivered to the patient.

In the illustrated embodiment, conduit 38 in patient circuit 36 has one end coupled to the output of the pressure/flow generator 42 and another end coupled to patient interface device 40. Conduit 38 is any tubing capable of carrying the gas flow from the pressure generator to the airway of the patient. Typically, a distal portion of the conduit relative to pressure/flow generator 42 is flexible to allow for freedom of movement of the patient. It is to be understood that various components may be provided in or coupled to patient circuit 36. For example, a bacteria filter, pressure control valve, flow control valve, sensor, meter, pressure filter, humidifier and/or heater can be provided in or attached to the patient circuit. Likewise, other components, such as muffler and filters can be provided at the inlet of pressure generator 42 and at the outlet of valve 32.

Patient interface device 40 in patient circuit 36 is any device suitable for communicating an end of conduit 38 with the airway of the patient. Examples of suitable patient interface devices include a nasal mask, oral mask or mouthpiece, nasal/oral mask, nasal cannula, trachea tube, intubation tube, hood or full face mask. It is to be understood that this list of suitable interface devices is not intended to be exclusive or exhaustive.

In the single limb patient circuit of the present invention, exhaled gas from the patient typically exits the patient circuit via an exhaust vent 43, as indicated by arrow D. In the illustrated embodiment, exhaust vent 43 is provided on a distal portion of conduit 38. Depending on the tidal volume of the patient and the pressure delivered by fluid delivery system 30, a small percentage of the exhaled gas may travel back up the conduit into fluid delivery system 30 and may even be exhausted to atmosphere through the gas inlet of the pressure generator and/or through a pressure/flow control valve 32, if such a valve is being used with the pressure generator.

Typically, exhaust vent 43 is an orifice provided in the conduit that communicates the interior of the conduit with atmosphere, with no active control over the flow of gas from the system. It is to be understood, however, that a wide variety of exhaust devices and configurations are contemplated for use with the pressure generating system of the present invention. For example, U.S. Pat. No. 5,685,296 to Zdrojkowski et al. discloses an exhalation device and method where the exhalation flow rate through the device remains substantially constant over a range of pressures in the patient circuit. This exhalation device, which is commonly referred to as a plateau exhalation valve or PEV, is suitable for use with the fluid delivery system of the present invention.

As shown in FIG. 1, fluid delivery system 30 includes a monitoring system, generally indicated at 44, to monitor the flow and pressure of gas delivered to the patient. In the illustrated embodiment, monitoring system 44 includes a flow sensor 46 that measures a rate at which the breathing gas flows within patient circuit 36. The present invention contemplates that any suitable sensor, such as a conventional pneumatach, can be used for flow sensor 46. It is to be further understood that flow sensor 46 need not be coupled directly to conduit 38. On the contrary, the present invention contemplates the use of any sensor or a plurality of sensors that can quantitatively measure airflow in the patient circuit. For example, flow in the system can be measured at the patient interface device or can be measured or estimated from the motor or piston speed or from torque used to provide the elevated pressure by pressure generator 42. In short, the present invention contemplates any conventional technique for measuring the flow of gas delivered to the patient.

Monitoring system 44 also includes a pressure sensor 48 that detects the pressure of the gas at the patient. In the illustrated embodiment, pressure sensor 48 is in fluid communication with patient interface device 40 via conduit 38. In this embodiment, the pressure at the patient is estimated based on the known pressure drop that occurs in conduit 38. It is to be understood, however, that the patient pressure can be measured directly at patient interface device 40.

Fluid delivery system 30 includes a controller 50, which is preferably a microprocessor capable of implementing a stored algorithm, that receives the monitored variables, typically from flow sensor 46 and pressure sensor 48, and controls pressure generating system 34 based on these signals. Of course, controller 50 includes the necessary memory and processing capability to implement the features of the present invention. For example, controller 50 controls the actuating energy provided to the pressure/flow control valve in a feedback fashion based on the output of the flow sensor, the pressure sensor, or both.

The present invention further contemplates that fluid delivery system 30 includes an input/output interface 52 for communicating, information, data and/or instructions and any other communicatable items, collectively referred to as "data", between a user and controller 50. Examples of common input/output interfaces suitable for this purpose include a keypad and display. Other communication techniques, either hard-wired or wireless, are also contemplated by the present invention. For example, the present invention contemplates providing a smart card terminal that enables data to be loaded into controller 50 from the smart card or loaded onto the smart card from the controller. Other exemplary, interface devices and techniques adapted for use with the fluid delivery system include, but are not limited to, an RS-232 port, CD reader/writer, DVD reader/writer, RF link, modem (telephone, cable or other). In short, any conventional technique for providing, receiving, or exchanging data with controller are contemplated by the present invention as input/output device 52.

Controller 50 also performs conventional leak estimation and respiratory cycle monitoring techniques. The present invention contemplates using any conventional technique for calculating leak $Q_{leak}$, which is the leakage of gas from the fluid delivery system and includes intentional leaks from the exhaust vent and unintentional leaks from the mask-patient interface, for example. The present invention also contemplates using any conventional technique for taking leak into consideration when determining the patient flow $Q_{patient}$, which is the flow of gas at the airway of the patient, and total flow $Q_{total}$, which is the flow of gas flow sensor 46. For example, U.S. Pat. Nos. 5,148,802 to Sanders et al. 5,313,937 to Zdrojkowski et al., 5,433,193 to Sanders et al., 5,632,269 Zdrojkowski et al., 5,803,065 to Zdrojkowski et al., and 6,029,664 to Zdrojkowski et al., and U.S. Pat. No. 6,536,432 to Truschel, 6,920,875 to Frank et al., and 6,626,175 to Jafari et al., the contents of each of which are incorporated by reference into the present invention, all teach techniques for detecting and estimating leak and managing the delivery of breathing gas to the patient in the presence of leaks.

The present invention also contemplates using any conventional technique for detecting the inspiratory and expiratory phases of the patient's respiratory cycle. For example, U.S. Pat. Nos. 5,148,802 to Sanders et al., 5,313,937 to Zdrojkowski et al., 5,433,193 to Sanders et al., 5,632,269 to Zdrojkowski et al., 5,803,065 to Zdrojkowski et al., and 6,029,664 to Zdrojkowski et al., and pending U.S. Pat. No. 6,626,175 to Jafari et al., all teach techniques for differentiating between the inspiratory and expiratory phases of a respiratory cycle.

It can be appreciated that FIG. 1 depicts a single-limb fluid delivery system, which is particularly well suited for providing a non-invasive pressure support therapy to a patient. However, the pressure/flow control valve of the present invention is also equally suited for use in a dual-limb ventilation system, which is typically used in an invasive, life support ventilator. A dual limb system is generally similar to the single limb system of FIG. 1 except that the patient circuit includes an inspiration branch and an expiration branch coupled to the patient interface. Pressurized gas is carried by the inspiration branch, which does not include an exhaust vent, from the pressure generating system to the patient. Gas expelled from the patient is carried by the expiration branch a gas flow exhaust system, which typically includes a pressure sensor, an exhaust flow control valve, and an exhaust flow sensor. Optionally, the gas flow exhaust system can include a bacteria filter that is operative when heated to a suitable operating temperature for capturing bacteria contained in the exhaled gas received from patient via the expiration branch.

Referring now to FIGS. 2-5B, the basic principle and the exemplary embodiment of the pressure/flow control valve of the present invention, which is suited for use in the above-described fluid delivery system, will be discussed. The operation of the pressure/flow control valve of the present invention is based on utilizing the repulsive magnetic force between two or more magnetic monopoles as a dampening and compensatory feature to enhance controllability and stability of the moving portions of the valve. The resistive magnetic force serves as a non-linear, and, more specifically, an asymptotic damper for sudden and fast jerks caused by stick-slip or inordinate overshoots generated by unavoidable excess input (acceleration command).

According to the Coulomb's Law, the force (F) of attraction or repulsion between two magnetic poles is inversely proportional to the square of the distance (x) between the two poles. This relationship is summarized as follows:

$$F = \left(P1 * \frac{P2}{\mu}\right) * \left(\frac{1}{x^2}\right), \quad (1)$$

where P1 and P2 are the magnetic strengths of the monopoles, x is the distance between the poles, and μ is the magnetic permeability.

Differentiating this relationship with respect to time yields, $$\text{Time rate of change of force} = \dot{F} = -2 * \left(P1 * \frac{P2}{\mu}\right) * \left(\frac{\dot{x}}{x^3}\right), \quad (2)$$

where $\dot{x}$=velocity. Thus, the interacting force between two magnetic monopoles changes asymptotically with respect to the distance between them. Further, the rate of change of force with time is directly proportional to velocity and inversely proportional to the third power of distance. Therefore, as two monopoles approach each other, the repulsive force grows asymptotically with respect to separating distance and velocity.

Figure 2:
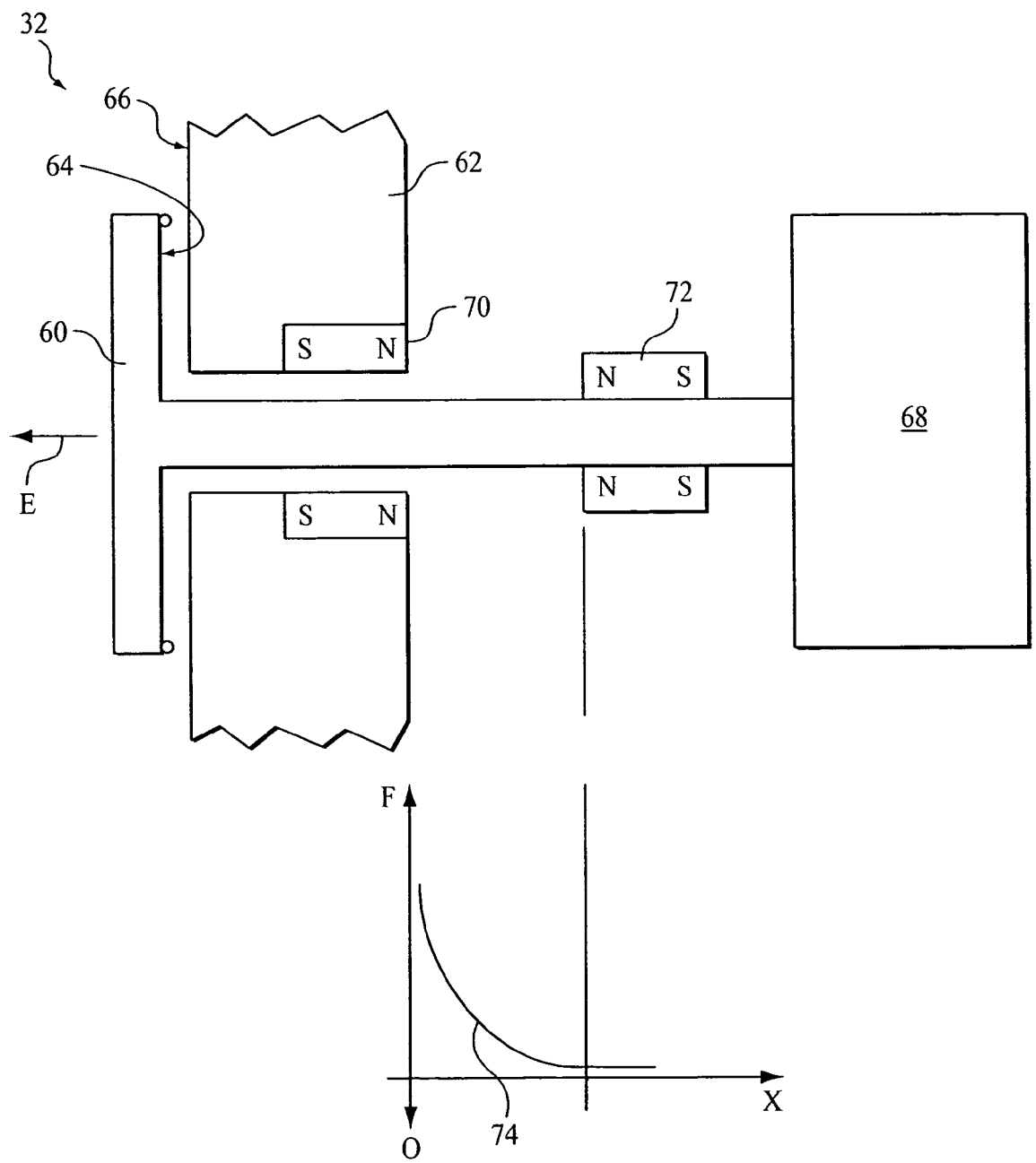
FIG. 2 is a schematic illustration of a first embodiment of a pressure/flow control valve and its operation according to the principles of the present invention.

The present invention utilizes this property to dampen the movement of one or more components of the pressure/flow control valve and to control the position of one or more components relative to other components. An example of this is illustrated in FIG. 2, which shows a first embodiment of a pressure/flow control valve 32 that includes a movable poppet type valve member 60 and stationary valve member 62. A valve seal is created between a surface 64 of moveable member 60 and a surface 66 of stationary member 62. Movement of moveable member 60 away from stationary member 62, as indicated by arrow E opens the valve, and further movement opens the valve even wider. An actuator 68, in combination with the interaction of the magnets, controls the position of moveable member 60 relative to stationary member 62.

A first magnet 70 is coupled to stationary member 62 and a second magnet 72 is coupled to movable member 60. Magnets 70 and 72 can be either permanent magnets or electromagnets. These magnets are oriented relative to one another such that a repulsive force (F) between the first magnet and the second magnet increases asymptotically, as indicated by curve 74, as the second magnet moves toward the first magnet, i.e., as the moveable member move in the direction indicated by arrow E. In this embodiment, movement in the direction indicated by arrow E increases a size of the valve opening.

The non-linear distance/force relationship causes moveable member 60 to move to a certain and fixed position relative to stationary member 62 when a given amount of actuating energy supplied to actuator 68. This occurs because the given amount of actuating energy produces a corresponding given amount of actuating force that urges moveable member 60 in direction E. This amount of actuating force will be offset and counterbalanced by the repulsive force between the two magnets at some distance x between the two magnets. Thus, for every amount of energy provided to actuator 68 (or force imparted on moveable member 60) there will be a corresponding static equilibrium location to which the moveable member will be move and remain so long as that same amount of energy (or force) is supplied to the actuator. In essence, the magnets make it possible to convert an actuating force imparted on the moveable member into a relative position between the moveable member and the stationary member.

When a constant amount of actuating energy is provided to the actuator in the pressure/flow control valve of the present invention, overshot of the moveable member from its corresponding static equilibrium position is strongly dampened due to the non-linear and increasing repulsive force imparted on the moveable member. It can be further appreciated that the static equilibrium position of the valve can be highly controlled based on the amount of actuating force imparted on the moveable member, i.e., the amount of actuating energy provided to the actuator, and the position and strength of the magnets.

Without the magnets, the given amount of actuating force would move the moveable member in direction E, but there would be not control over the position of the moveable member relative to the stationary member and not way to prevent overshot is a particular position is desired. Moreover, if a linear dampening force is applied to the moveable member, the would be some dampening of the moveable member, but its position relative to the stationary member would be unknown.

By providing this non-linear distance/force relationship between the moveable member and the stationary member in the pressure/flow control valve, the present invention enhances the controllability and the responsiveness of this force-actuated motion control system even with uncertain (unmeasured) time-variant dynamics and moving part stickslip. While the distance/force relation between the moveable member and the stationary member is described above as being asymptotic, it is to be understood that the present invention contemplates using any non-linear distance force relationship.

A second embodiment of a pressure/flow control valve 78 is shown in FIGS. 3A-4B. Valve 78 includes many features in common with the valve described in U.S. Appln. No. 09/347,071 to TRUITT et al., now U.S. Pat. No. 6,615,831, which is assigned to the assignee of the present invention, the contents of which are also hereby incorporated herein by reference. Valve 78 is defined by a number of parts, including a hollow, first or inner cylinder 80, which includes a center barrel 82, a first barrel 84, and a second barrel 86. Cylinder 80 forms the stationary member of valve 78.

First barrel 84 and second barrel 86 are positioned at opposite ends of center barrel 82 and coaxially therewith. Inner cylinder 80 has an open first end 88, an open second end 90, a first slot 92 defined in a wall of second barrel 86, and a second slot 94 defined in the wall of second barrel 86 between first slot 92 and second end 90. A separating plate 96 is positioned in inner cylinder 80 and, more particularly, in second barrel 86, between first slot 92 and second slot 94 for obstructing or prevent flow of gas therebetween. An annular permanent magnet 98 is secured around an end of center barrel 82 opposite first barrel 84 as part of an actuating system for opening and closing slots 92 and 94.

Pressure/flow control valve 78 also includes a second or outer cylinder 100 configured to be received around magnet 98 and inner cylinder 80 and to move axially between first end 88 and second end 90 of inner cylinder 80. Thus, outer cylinder 100 defines the movable member of valve 78. Outer cylinder 100 includes a third slot 102 defined in the wall thereof. In an assembled configuration, first slot 102 is capable of overlapping first slot 92 and second slot 94 individually or simultaneously.

A coil 104, such as a voice coil, is secured around outer cylinder 100 in magnetic flux coupled relation with magnet 98. The present invention contemplates that coil 104 can be attached to the end of the portion of the outer cylinder or wound around the outer cylinder. A wire 105 extends from coil 104 for passing a current through the coil. Coil 104 is configured to receive DC current from controller 50.

Figure 3A:
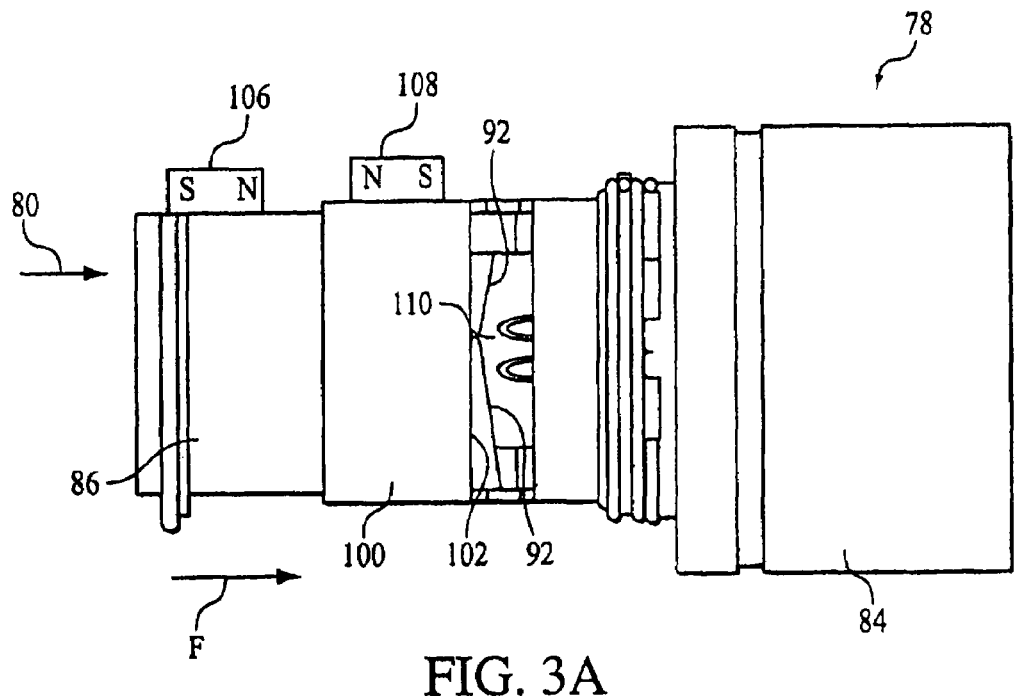
FIGS. 3A and 3B are side and sectional views, respectively, of a second embodiment of a pressure/flow control valve showing a moveable outer cylinder in a first position relative to a stationary inner cylinder.

According to one embodiment of the present invention, in response to receiving DC current of a first polarity, coil 104 urges outer cylinder 100 axially relative to inner cylinder 80 in a first direction indicated by arrow F in FIG. 3A. When displaced to the maximum amount possible in the first direction, first slot 102 in outer cylinder 100 and blower discharge slot 92 in inner cylinder 80 are aligned and outer cylinder 100 obstructs exhaust intake slot 94 of inner cylinder 80.

Figure 3B:
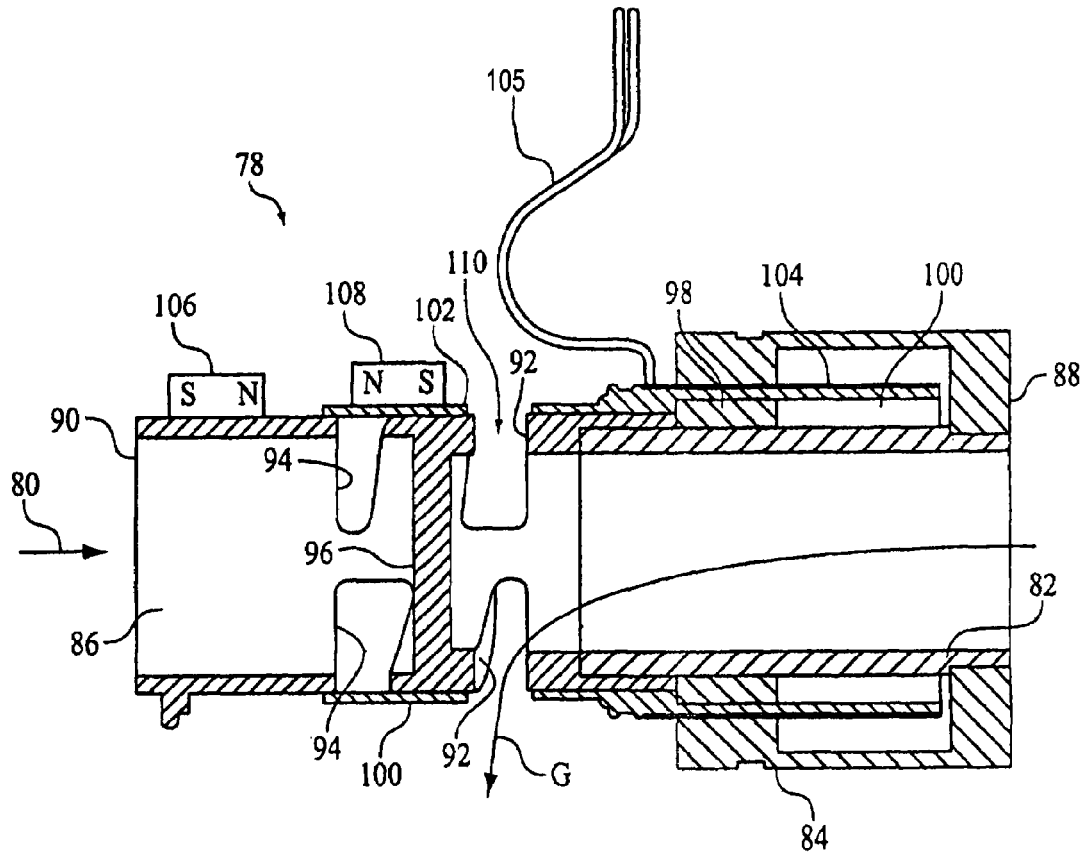

FIGS. 3A and 3B illustrate outer cylinder 100 displaced as far as possible in the first direction with third slot 102 and first slot 92 being generally aligned with one another so that gas flows through valve 78 as indicated by arrow G. In an exemplary embodiment of the present invention, first end 88 of valve 78 is operatively coupled to the pressure generator, so that in the embodiment shown in FIGS. 3A and 3B, gas flows from the pressure generator out of an aperture 110 defined by the overlap of third slot 102 and first slots 92. In addition, the present invention contemplates arranging the connection of valve 78 to the patient circuit such that gas exiting the valve through aperture 110 is communicated to the patient circuit. Thus, movement of outer cylinder 100 relative to inner cylinder 80 changes the size of aperture 110 to control a degree of restriction for the flow of gas 108 from the pressure generator to the patient circuit.

Figure 4A:
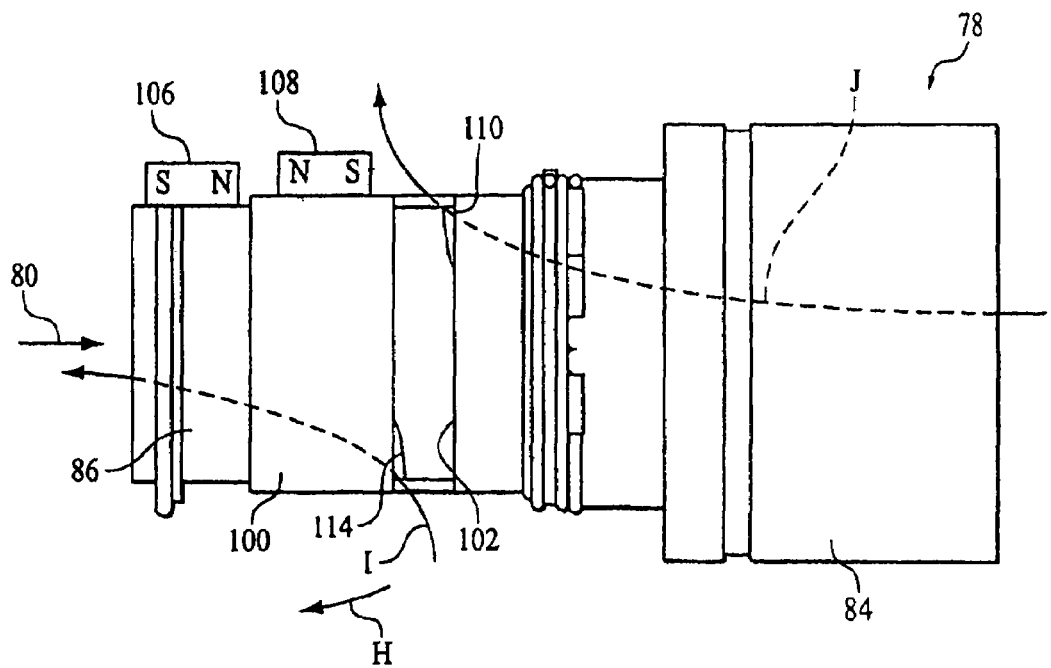
FIGS. 4A and 4B are side and sectional views, respectively, of the pressure/flow control valve of FIGS. 3A and 3B showing the outer cylinder in a second position relative to the inner cylinder.
Figure 4B:
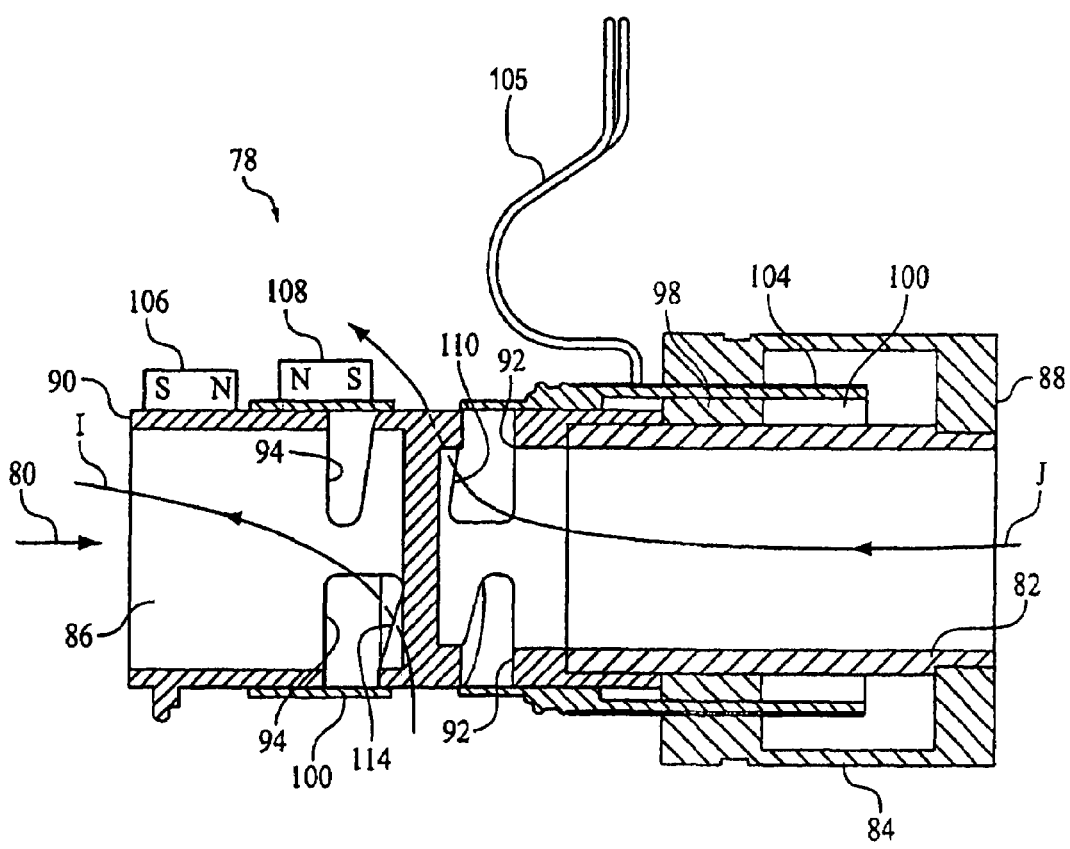

Similarly, in response to receiving DC current of a second polarity, opposite the first polarity, coil 104 urges outer cylinder 100 axially relative to inner cylinder 80 in a second direction opposite the first direction, as indicated by arrow H in FIG. 4A. When displaced to the maximum amount possible in the second direction, third slot 102 of outer cylinder 100 and second slot 94 of inner cylinder 80 align and outer cylinder 100 at least partially obstructs first slot 92 of inner cylinder 80. In addition, third slot 102 in outer cylinder 100 and second slot 94 in inner cylinder 80 are aligned to define an aperture 114. As a result, gas flows, as indicated by arrow I, into second barrel 86 through an aperture 114 defined by the overlap of third slot 102 and second slot 94. This flow of gas can be vented to atmosphere, either directly or through a muffler, or it can be communicated to the intake of the pressure generator. Movement of outer cylinder 100 relative to inner cylinder 80 changes the size of the aperture 114 to control a degree of restriction for the flow of gas from the second conduit. Because slot 92 is also only partially obstructed in this embodiment, gas also flows, as indicated by arrow J, through valve 78, i.e., from within inner cylinder 80 through aperture 110.

In this exemplary embodiment, a first magnet 106 is disposed on inner cylinder 80 and a second magnet 108 is disposed on outer cylinder 100. To control the movement of the cylinder 80 relative to outer cylinder 100, first and second magnets 106 and 108 are oriented relative to one another such that a repulsive force between the first magnet and the second magnet increases asymptotically as the second magnet moves toward the first magnet, i.e., as the size of opening 114 increases and the size of opening 110 decreases.

It can be appreciated that the coupling of the valve within the patient circuit, the orientation of the magnets (i.e., the repulsive or attractive force orientation), and the flow of an actuating current in coil 104, can be arranged in a number of different configurations depending on how the valve is to be used an controlled.

FIGS. 5A and 5B are side views and a sectional view of a pressure/flow control valve 120 according to a third embodiment of the present invention. In this embodiment, pressure/flow control valve 120 includes a housing 122 enclosing inner cylinder 80 and outer cylinder 100. In this embodiment, gas flows into a chamber 124 defined between housing 122 and outer cylinder 100 through an inlet port 126 defined in the side of housing 122, as indicated by arrow K.

In the deactivated position, which corresponds to the position of outer cylinder 100 and inner cylinder 80 shown in FIGS. 3A and 3B, the outer cylinder unblocks first slot 92 and blocks second slot 94, so that gas flows from chamber 124 through a bypass port 128, as indicated by arrow L, and does not flow to the patient. When coil 104 is energized, outer cylinder 100 moves in a direction indicated by arrow M to at least partially obstruct port 92 and unblock second slot 94, so that gas from chamber 124 through second slot 94 to a patient, as indicated by arrow N. Depending on the degree of obstruction of first slot 92, gas can be prevented from flowing to bypass port 128. See, e.g., FIGS. 4A and 4B of the present application.

In this embodiment, a first magnet 106' is coupled to housing 122 and a second magnet 108' is coupled to outer cylinder 100. First magnet 106' and second magnet 108' are oriented such that second magnet 108' moves toward first magnet 106' as outer cylinder 100 moves in a direction indicated by arrow M. In addition, second magnet 108' and first magnet 106' are oriented relative to one another such that movement of second magnet 108' toward first magnet 106' increases the repulsive force between the first magnet and the second magnet asymptotically as the second magnet moves toward the first magnet. In addition, movement of the second magnet toward the first magnet, i.e., movement of outer cylinder 100 relative to inner cylinder 80 in a direction M increases a size of the opening over port 94 so that more gas flow toward the patient from inlet port 126.

In an exemplary embodiment of the present invention a constant activating energy is provided to the actuating elements of the valve to produce a constant actuating force urging outer cylinder 100 in direction M, which is then offset by a corresponding repulsive force between first magnet 106' and second magnet 108' so as to maintain the outer cylinder at a static equilibrium position relative to the inner cylinder. In a further preferred embodiment, this static equilibrium position corresponds to a position in which second slot 94, i.e., the slot or port through which gas flows to the patient, is maintained blocked or is unblocked only slightly to minimize the flow of gas to the patient and all other gas flow through first slot 92 and follows the bypass path indicated by arrow L.

It can be appreciated that the present invention provides an effective configuration that utilizes the repulsive magnetic force between two magnetic monopoles for generating an asymptotically increasing (or decreasing) compensating force based on the distance between them. The repulsive magnetic force between two monopoles is inversely proportional to the square of distance between them. Further, the time rate of change of the repulsive force is directly proportional the velocity of movement and inversely proportional to the third power of the distance between the monopoles. This allows the position of one member to be controlled based on the actuating energy or force provided on that member and prevents or minimized overshot.

In contrast, a mechanical spring used as a damper generates a linear resistive force proportional to distance and velocity, which can be summarized as follows:

$$F = K*x, \text{ and} \quad (3)$$

$$\dot{F} = K*\dot{x}, \quad (4)$$

where K is the spring constant. Thus, the magnetic compensator of the present invention is much more effective and faster dampener than a spring damper, because it provides an asymptotic resisting force (compared with a linear resistive force in case of a mechanical spring) with respect to displacement as well as an asymptotic rate of force change (compared with a linear relation in case of a mechanical spring) that in addition changes inversely with the third power of distance. Thus, the proposed invention enhances the controllability and responsiveness of force-actuated motion control systems with uncertain (unmeasured) time-variant dynamics and moving part stick-slip.

Significant advantages of the asymptotic force dampening provided by the pressure/flow control valve of the present invention is in the simplicity of the design and installation, the low cost, no moving parts, no mechanical wear, and very fast and asymptotic response providing enhanced controllability and stability. This simplifies the signal processing and control algorithms need to control the position of the moving member relative to the stationary member and eliminates the need for friction modeling and computation-heavy state estimation and adaptive control algorithms requiring modeling and online measurement of changing patient characteristics and system dynamics.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A fluid delivery system comprising:
  (a) a pressure generating system adapted to generate a flow of gas at a pressure level;
  (b) a patient circuit having a first end coupled to the pressure generating system and a second end adapted to be coupled to an airway of a patient; and
  (c) a valve operatively associated with the patient circuit to control a pressure, a flow of gas, or both in the patient circuit, wherein the valve comprises:
    (1) a first valve member,
    (2) a second valve member operatively coupled to the first valve member and moveable relative thereto, wherein the first valve member and the second valve member cooperate to define a valve opening having a size that varies with a relative position between the first valve member and the second valve member to control the pressure, the flow of gas or both,
    (3) a first magnet coupled to the first valve member, and
    (4) a second magnet coupled to the second valve member and magnetically coupled to the first magnet such that a magnetic interaction of the first magnet and the second magnet provides a dampening force between the first valve member and the second valve member, and (5) wherein the first magnet and the second magnet are oriented relative to one another such that a repulsive force between the first magnet and the second magnet increases non-linearly as the second magnet moves toward the first magnet, and further comprising: an actuator associated with the first valve member and the second valve member, wherein the actuator advances the second valve member relative to the first valve member such that second magnet moves toward the first magnet; and a controller coupled to the actuator, wherein the controller provides an actuating energy supplied to the actuator that imparts an actuating force on the second valve member urging the second magnet toward the first magnet.

2. The system of claim 1, wherein the second valve member is a sleeve and the first valve member is a conduit.

3. The system of claim 1, wherein the first valve member is a stationary member and the second valve member is a moveable member.

4. The system of claim 1, wherein the first magnet and the second magnet are oriented relative to one another such that a repulsive force between the first magnet and the second magnet increases asymptotically as the second magnet moves toward the first magnet.

5. The system of claim 4, wherein movement of the second magnet toward the first magnet increases a size of the valve opening to increase at least one of the pressure and a flow of gas in the patient circuit.

6. The system of claim 4, further comprising an actuator coupled to the first valve member, wherein the actuator advances the second valve member relative to the first valve member such that second magnet moves toward the first magnet.

7. The system of claim 6, wherein the actuator includes a coil coupled to the second valve member that moves the second valve member toward the first valve member responsive to an actuating energy being provided to the coil.

8. The system of claim 1, further comprising at least one of a pressure sensor and a flow sensor coupled to the patient circuit so as to measure a pressure and a flow, respectively, of the gas in the patient circuit, wherein the controller provides the actuating energy to the actuator based on an output of at least one of the pressure sensor and the flow sensor.

9. The system of claim 1, wherein, during operation of the fluid delivery system, the controller provides a constant actuating energy to the actuator that imparts a first actuating force on the second valve member to maintain the second valve member at a static equilibrium position relative to the first valve member that corresponds to a relative position between the first valve member and the second valve member, where the first actuating force is equal to the repulsive force between the first magnet and the second magnet.

10. A fluid delivery system comprising:
(a) a pressure generating system adapted to generate a flow of breathing gas at a pressure level;
(b) a patient circuit having a first end coupled to the pressure generating system and a second end adapted to be coupled to an airway of a patient; and
(c) a valve operatively connected to the patient circuit to control one of a pressure and a flow of gas in the patient circuit, wherein the valve comprises:
(1) a first valve member,
(2) a second valve member associated with the first valve member such that the first valve member is moveable relative to the second valve member, wherein the first valve member and the second valve member cooperate to define a valve opening having a size that varies with a relative position between the first valve member and the second valve member, and wherein the size of the valve opening controls a pressure or a flow of gas provided to the patient,
(3) an actuator associated with the first valve member and the second valve member, wherein the actuator is adapted to provide an actuating force on the second valve member that moves the second valve member toward the first valve member to change the size of the valve opening, and
(4) movement controlling means for providing a dampening force that prevents movement of the second valve member toward the first valve member, wherein the dampening force increases non-linearly as the second valve member moves toward the first valve member.

11. The system of claim 10, wherein the movement controlling means comprises a first magnet operatively coupled to the first valve member and a second magnet operatively coupled to second valve member, wherein the first magnet is a permanent magnet or an electromagnet, and wherein the second magnet is a permanent magnet or an electromagnet.

12. The system of claim 11, wherein the first magnet and the second magnet are oriented relative to one another such that a repulsive force between the first magnet and the second magnet increases asymptotically as the second magnet moves toward the first magnet.

13. The system of claim 10, wherein the second valve member is a sleeve and the first valve member is a conduit.

14. The system of claim 13, wherein the conduit comprises a hollow first cylinder having an open first end, an open second end, a blower discharge slot defined in a wall thereof, an exhaust discharge slot defined in the wall thereof between the blower discharge slot and the second end, and a separating plate positioned in the first cylinder between the exhaust discharge slot and the blower discharge slot, and wherein the sleeve comprises a hollow second cylinder having a first slot defined in a wall thereof, with the second cylinder positioned coaxially around the first cylinder.

15. The system of claim 10, further comprising controlling means associated with the actuator for controlling the actuating force imparted by the actuator on the second valve.

16. The system of claim 15, further comprising at least one of a pressure sensor and a flow sensor coupled to the patient circuit so as to measure a pressure and a flow, respectively, of the gas in the patient circuit, wherein the controlling means controls the actuating force based on an output of at least one of the pressure sensor and the flow sensor.

17. The system of claim 10, wherein, during operation of the fluid delivery system, the actuator produces a constant actuating force that is offset by a corresponding repulsive force between the first magnet and the second magnet so as to maintain the second valve member at a static equilibrium position relative to the first valve member.

18. A method of controlling pressure or flow in a fluid delivery system comprising:
providing a first valve member and a second valve member associated with the first valve member such that the first valve member is moveable relative to the second valve member, and wherein the first valve member and the second valve member cooperate to define a valve opening having a size that varies with a relative position between the first valve member and the second valve member to control a pressure or a flow of gas delivered to the patient;
providing an actuating force on the second valve member to move the second valve member toward the first valve member to change the size of the valve opening; and
controlling movement of the second valve member toward to the first valve member by providing a dampening force that prevents movement of the second valve member toward the first valve member, wherein the dampening force increases non-linearly as the second valve member moves toward the first valve member.

19. The method of claim 18, wherein controlling movement of the second valve member includes providing a first magnet operatively coupled to the first valve member and a second magnet operatively coupled to second valve member, wherein the first magnet and the second magnet are oriented relative to one another such that a repulsive force between the first magnet and the second magnet increases asymptotically as the second magnet moves toward the first magnet.

20. The method of claim 18, wherein movement of the second magnet toward the first magnet increases a size of the valve opening to increase at least one of the pressure and a flow of gas delivered to a patient.

21. The method of claim 18, further comprising monitoring at least one of a pressure and a flow of gas delivered to such a patient and controlling the actuating force based on at least one of the pressure and the flow of gas delivered to such a patient.

22. The method of claim 18, wherein providing an actuating force includes providing a biasing actuating force that is offset by the repulsive force between to maintain the second valve member at a static equilibrium position relative to the first valve member.

* * * * *